(12) United States Patent
Schmeink et al.

(10) Patent No.: US 11,688,490 B2
(45) Date of Patent: *Jun. 27, 2023

(54) METHOD AND MODULE FOR LINKING DATA OF A DATA SOURCE TO A TARGET DATABASE

(71) Applicant: KONINKLIJKE PHILIPS N.V., Eindhoven (NL)

(72) Inventors: Anke Schmeink, Aachen (DE); Sandra Geisler, Aachen (DE); Andreas Brauers, Iserlohn (DE); Christoph Josef Quix, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

This patent is subject to a terminal disclaimer.

(21) Appl. No.: 17/110,605

(22) Filed: Dec. 3, 2020

(65) Prior Publication Data

US 2021/0090692 A1 Mar. 25, 2021

Related U.S. Application Data

(63) Continuation of application No. 13/132,945, filed as application No. PCT/IB2009/055537 on Dec. 7, 2009, now Pat. No. 10,878,945.

(30) Foreign Application Priority Data

Dec. 12, 2008 (EP) .................................. 08171430

(51) Int. Cl.
*G06F 16/25* (2019.01)
*G16H 10/20* (2018.01)

(52) U.S. Cl.
CPC ............. *G16H 10/20* (2018.01); *G06F 16/25* (2019.01)

(58) Field of Classification Search
CPC ........ G06F 16/367; G06F 40/30; G06F 16/86; G06F 16/284; G06F 16/25; G06F 16/2423; G06F 16/3338; G06F 16/23; G06F 16/28; G16H 10/20
See application file for complete search history.

(56) References Cited

U.S. PATENT DOCUMENTS

| | | | |
|---|---|---|---|
| 7,328,209 B2 | 2/2008 | Das et al. | |
| 7,930,293 B2 | 4/2011 | Fox et al. | |
| 2002/0023091 A1 | 2/2002 | Silberberg et al. | |
| 2003/0120665 A1* | 6/2003 | Fox | G06F 16/25 707/999.1 |
| 2005/0097628 A1 | 5/2005 | Lussier et al. | |
| 2005/0149484 A1 | 7/2005 | Fox et al. | |
| 2005/0203920 A1 | 9/2005 | Deng et al. | |
| 2006/0178862 A1 | 8/2006 | Chan et al. | |
| 2007/0130206 A1 | 6/2007 | Zhou et al. | |
| 2007/0150495 A1 | 6/2007 | Koizumi et al. | |
| 2007/0226246 A1 | 9/2007 | Dheap et al. | |
| 2008/0040308 A1 | 2/2008 | Ranganathan et al. | |
| 2008/0082574 A1* | 4/2008 | Hosokawa | G06F 16/258 707/999.103 |
| 2009/0077531 A1* | 3/2009 | Miloslavsky | G06F 8/10 717/100 |
| 2010/0121885 A1* | 5/2010 | Hosomi | G06F 16/367 707/794 |
| 2010/0228782 A1* | 9/2010 | Rao | G06F 16/367 707/794 |

FOREIGN PATENT DOCUMENTS

| | | |
|---|---|---|
| EP | 1708099 A1 | 10/2006 |
| JP | 2003233528 A | 8/2003 |

OTHER PUBLICATIONS

Munir et al ("Ontology Assisted Query Reformulation using the Semantic and Assertion Capabilities of OWL-DL Ontologies"). (Year: 2008).*
Munir et al: "Ontology Assisted Query Reformulation Using the Semantic and Assertion Capabilities of Owl-DL Ontologies", IDEAS08, Sep. 2008, ACM, pp. 81-90.
Branson et al: "a Data Model for Integrating Heterogeneous Medical Data in The Health-e-Child Project", Healthgrid'08, Jun. 2008, Downloaded From http://arxiv.org/ftp/arxiv/papers/0812/0812.2874.pdf>; Retrieved Mar. 12, 2008, 10 Page Document.
Geisler, T.: Ontology-Based System for Clinical Trial Data Management, IEEE Benelux EMBS Symposium, Dec. 6-7, 2007, 4 Page Document.
Gruber, T.: "a Translation Approach to Portable Ontology Specification", Knowledge Acquisition, 1993, vol. 5, 24 Page Document.
Chong et al: "Ontology Based Metadata Management in Medical Domains"; Journal of Research and Practice in Information Technology, vol. 35, No. 2, May 2003, pp. 139-154.
Vargas-Vera et al: "a Knowledge-Based Approach to Ontologies Data Integration" Knowledge Media Institute(KMi), the Open University, United Kingdom, Tech Report kmi-04-17, 11 Page Document.
Wache et al: "Ontology-Based Integration of Information—A Survey of Existing Approaches"; Intelligent Systems Group, Center for Computing Technologies, University of Bremen, Bremen, Germany, 10 Page Document.
Gong et al: "an Ontology for the Integration of Multiple Genetic Disorder Data Sources"; Proceedings of the 2005 IEEE Engineering in Medicine and Biology 27th Annual Conference, Shanghai, China, Sep. 1-4, 2005, pp. 2824-2827.

* cited by examiner

*Primary Examiner* — Yuk Ting Choi

(57) ABSTRACT

A method is provided. The method comprises accessing a target database comprising at least one table associated with a first concept or property of a reference ontology, defining a data source ontology for a data source comprising a dataset, said data source ontology comprising a second concept or property, wherein said second concept or property is different from said first concept or property, and creating a link between said second concept or property and said first concept or property, said link defining to which table of said target database data of said dataset, associated with said second concept or property, is related.

11 Claims, 4 Drawing Sheets

METHOD AND MODULE FOR LINKING DATA OF A DATA SOURCE TO A TARGET DATABASE

RELATED APPLICATIONS

This application is a continuation of U.S. patent application Ser. No. 13/132,945, filed on Jun. 6, 2011, which is the U.S. National Phase Application under 35 U.S.C. § 371 of International Application No. PCT/IB2009/055537, filed on Dec. 7, 2009, which claims the benefit and priority of European Application No. 08171430.5, filed on Dec. 12, 2008, the disclosures of which are hereby incorporated by reference in their entirety herein.

This invention relates to a method for linking data of a data source to a target database. More particularly, the invention relates to a method for integrating medical data into a database.

FIELD OF THE INVENTION

This invention relates to a method for linking data of a data source to a target database. More particularly, the invention relates to a method for integrating medical data into a database.

BACKGROUND OF THE INVENTION

Clinical trials are common in medical research to investigate new medications, medical devices and other medical products and their impact on the human being. Frequently, new studies are issued and the number of conducted clinical trials increases. For example, the study register of the U.S. National Institutes of Health, which is one of the most frequently used public databases for clinical studies, contained approximately 23,500 clinical studies in 2006. In January 2008, the registered trials had more than doubled to almost 50,000 studies from over 153 countries. Especially, the pharmaceutical industry and manufacturers of medical devices push the conduct of more and more studies.

With this increasing amount of data, there is a need for rapid, time efficient but also accurate study planning, conducting, and analysis of results is indispensable. Particularly, the data collected during clinical trials is valuable to the organizations controlling and executing the trials. Hence, the careful collection, handling, and storage of the data while obeying national and international regulations are a major task in clinical study management.

Companies in the field of medical technology are concerned with the development of novel medical devices, which contribute to the development and improvement of diagnostics, therapy, prevention and monitoring of diverse diseases. For this purpose clinical trials and preliminary pilot trials are conducted. During the trials, data of interest is acquired in various formats by means of the developed devices, by questionnaires, case report forms and more. Subsequently, the gathered data is processed and statistically analyzed to evaluate the quality and applicability of the novel devices. Furthermore, the coherence between acquired data and the disease progression as well as the health status of the patient is targeted. The results may be compared with data of devices, which are used in current medical practice or analyzed to gain new insights into certain disease progressions.

One way to manage clinical trials is to use ontologies. According to A Translation Approach to Portable Ontology Specification, Knowledge Acquisition 5:199-220, 1993, by Thomas Gruber, an ontology is a formal, explicit specification of a shared conceptualization. It describes a domain of interest in a machine readable and semantic way such that the concepts of the domain, relationships among them and constraints can be expressed such that a majority of a larger community agrees upon it.

Ontologies are used in the fields of artificial intelligence, knowledge engineering, and the Semantic Web and are developed for variety of domains, including biomedicine or physics.

The modeling and use of ontologies in the field of data integration offers several benefits. Ontologies describe domains on a high abstraction level. The strengths of ontologies lie especially in the possibility to build a consistent and formal vocabulary, which cannot only be used for the definition of the structure and meaning of data stored in a database, but also be reused, to interoperate with and build applications based on this vocabulary.

To make the trial data accessible at one central point for statistical analysis or preparation for the submission to respective authorities, it ideally needs to be integrated into a single database. Approaches in data integration can be distinguished according to different aspects. One aspect is the manifestation of integration of the data sources. This can be described with the terms on-demand integration, where data sources are integrated just when a user or system queries a framework of data sources. The requested data is then acquired from each data source separately and afterwards integrated into a single result. On the other hand, the in-advance integration copies, consolidates and integrates data from the data sources into a single database, which can be queried afterwards.

"Ontology-based system for clinical trial data management", IEEE Benelux EMBS Symposium, Dec. 6-7, 2007 of Geisler, S. et al describes an ontology based system for integration of clinical trial data management. A reference ontology serves as basis for both the generation of clinical trial databases and the integration of data from various data sources into this database.

However, such system suffers from low flexibility since the reference ontology must be known when defining the ontological representations of the data sources. Moreover, unnecessary work may be performed since in some cases only a minor amount of data of the data sources is of interest. In such cases, it is not effective to define ontologies for all data sources, as the ontologies have also to represent the mappings of the data sources to the target database. The editing of such complex ontologies is consequently infeasible for users.

Hence, an improved method for assembling data of a data source allowing for increased flexibility and time efficiency would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above-mentioned problems by providing a method, module, and computer program product according to the appended patent claims.

An object according to some embodiments is to provide a method facilitating an improved linking and integration of data.

Another object according to some embodiments is to provide a method for dynamically integrating data of a data source into a target database.

An idea according to some embodiments is to provide an ontology-based mapping between selected concepts and their properties of a reference ontology and various data source ontologies to facilitate in-advance data integration.

According to an aspect, a method is provided. The method comprises accessing a target database comprising at least one table associated with a first concept or property of a reference ontology, defining a data source ontology for a data source comprising a dataset, said data source ontology comprising a second concept or property, wherein said second concept or property is different from said first concept or property, and creating a link between said second concept or property and said first concept or property, said link defining to which table of said target database data of said dataset, associated with said second concept or property, is related.

Herein, the term "table" should be interpreted broadly to cover all equivalents for representing relations in the field of information technology and database modeling. The method could be implemented for several different applications, such as for integration of medical data of clinical trials. Moreover, the method could be implemented for any set of ontologies used in applications such as energy supply, financial applications, commerce applications, and different kinds of research projects wherein data from different sensors/devices is used.

According to an aspect, a module is provided. The module comprises a first unit for accessing a target database comprising at least one table associated with a first concept or property of a reference ontology, a second unit for defining a data source ontology for a data source comprising a dataset, said data source ontology comprising a second concept or property, wherein said second concept or property is different from said first concept or property, and a third unit for creating a link between said second concept or property and said first concept or property, said link defining to which table of said target database data of said dataset, associated with said second concept or property, is related.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment of the present invention applicable to a method of integrating data.

Figure 1:
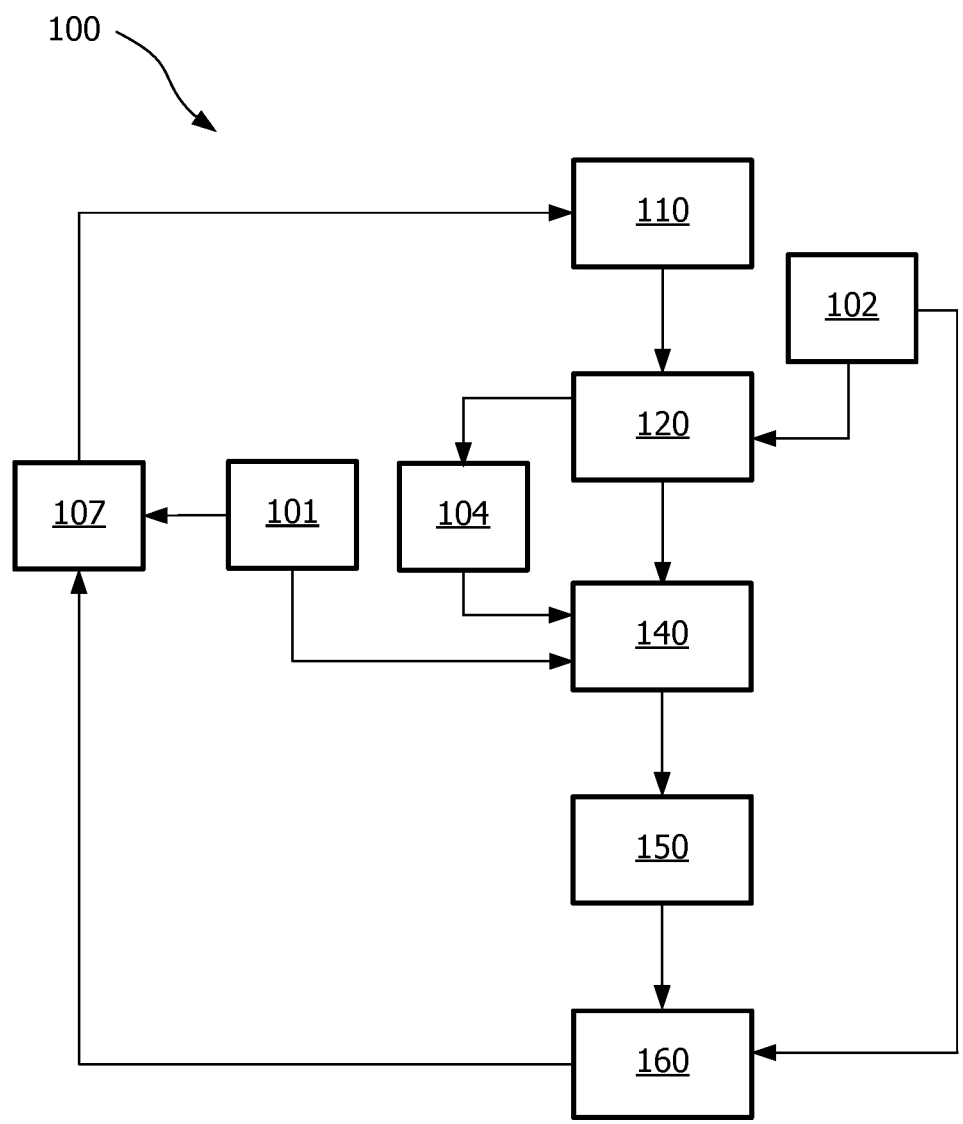
FIG. 1 is a flow chart schematically showing a method according to an embodiment.

With reference to FIG. 1, the method comprises accessing 110 a target database 107 comprising at least one table associated with a first concept or property of a reference ontology 101. Further, the method comprises defining 120 a data source ontology 104 for a data source 102 comprising a dataset, said data source ontology 104 comprising a second concept or property, wherein said second concept or property is different from said first concept or property. The method also comprises creating 140 a link between said second concept or property and said first concept or property, said link defining to which table of said target database data of said dataset, associated with said second concept or property, is related.

In the embodiment shown in FIG. 1, the method comprises storing 150 said link into a data integration module (not shown). The method also comprises storing 160 said data into the corresponding table of the target database 107, by utilizing the link.

In an embodiment, the target database 107 is defined by a selected first set of concepts and properties of the reference ontology 101.

Figure 2:
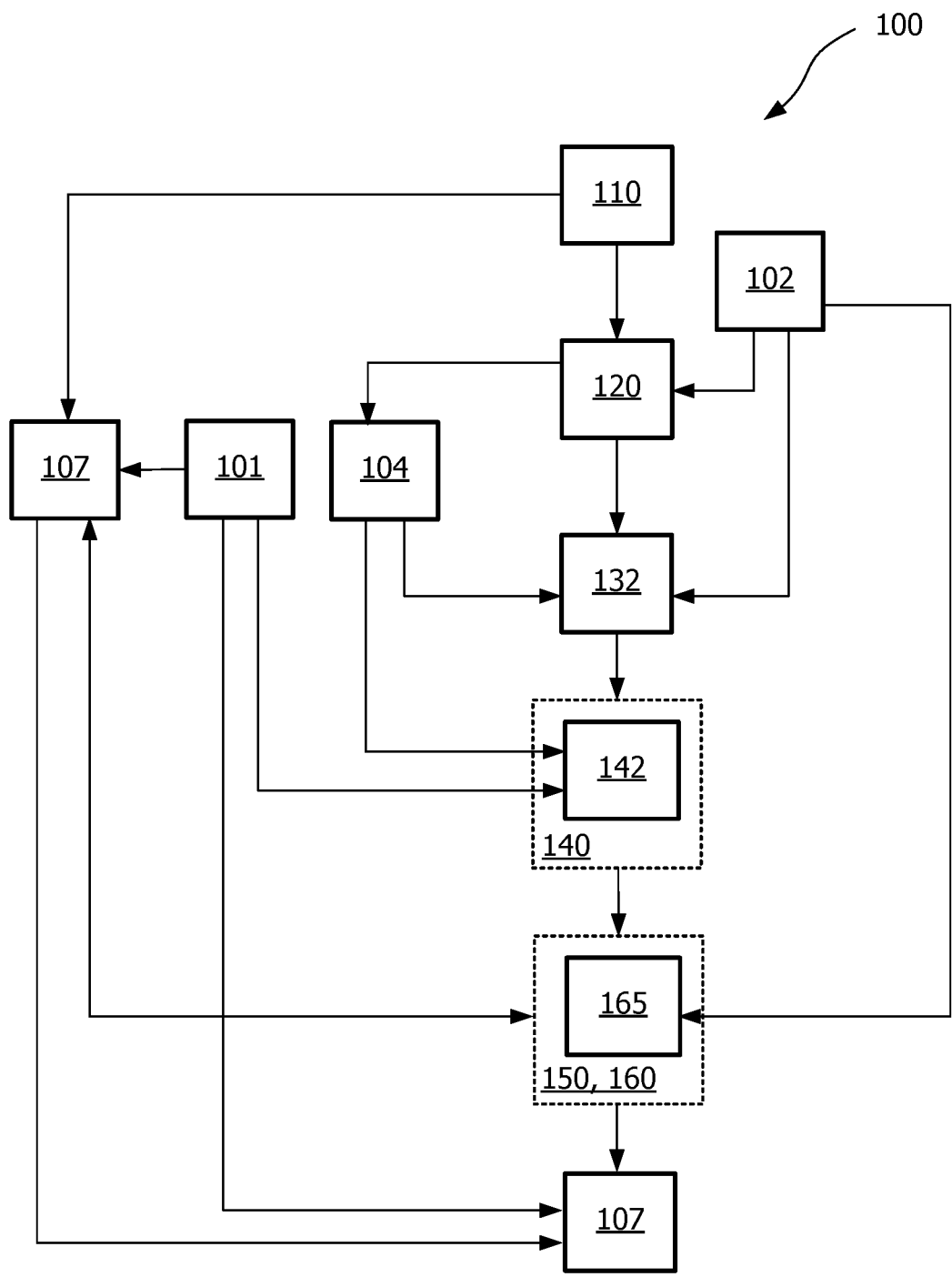
FIG. 2 is a flow chart schematically showing a method according to an embodiment.

In another embodiment, a method 100 is provided to integrate data of at least one data source according to another schema. As shown in FIG. 2, the method 100 comprises accessing 110 a target database 107 defined by a reference ontology 101. Also, a user interface (not shown) is provided for defining 120 a data source ontology 104 from a data source 102. This is provided by converting relational schema representations of the data source 102 to an ontology 104. The provision of a user interface is advantageous in that a user easily can adapt or create the ontological representations of the data sources. Following this, a meta representation is formed for linking 132 the ontological representation 104 of the data source with the relational representation 102 of the data source. During creation of a number of links 140 between the data source ontology 104 with respect to the reference ontology 101, pairs of properties of the ontologies 101, 104 are built 142. The step of creating 140 links comprises assembling a query for determining data to be extracted from the data sources, creating a data integration module, and storing 150 said links into the data integration module. Integration of data into the target database 107 is performed by executing the data integration module, i.e. by providing 165 a query for each table of the target database, retrieving data from one data source, and storing the retrieved data in the target database 107. Following this, a meta representation is formed for linking 170 the ontological representation 101 of the selected concepts and properties of the data target with the relational representation 107 of the data target.

The data source 102 and the data target 107 are described by separate ontologies, using different vocabulary.

Depending on the links between concepts or properties of two ontologies, data integration modules are assembled, i.e., processes to extract data from a data source and load them into a data target.

In an embodiment, a meta representation is linking the relational and the ontological representations 101, 104 of the data source 102 and the data target 107. In such embodiment, it is assumed that the data source 102 can be queried in a relational way. Hence, the data source 102 may be a relational database or an Excel workbook.

In an embodiment, linking the data target tables and the data source columns is performed in the following way. For each linked table in the target database 107, the columns of the data source 102 linked to columns of that database table are added to a list. This list is used to assemble a query on the data source 102, which retrieves all data from the columns of the data source 102. Each table of the target database 107 is then filled by executing the according queries for the data source 102. If a mapped data source property is linked to a foreign key column in a data source table, the according join between the table and the referenced table has to be made. Therefore, a user has to select an additional property, with which the join can be established. A join is also automatically inserted, when columns of two or more data target tables are mapped to the target table. If a data target property is mapped which represents a foreign key column, the respective ID is looked up in the referenced table by joining the target table and the referenced table using an additional user defined property representing a data target column.

In an embodiment, the Clinical Trial Data Management Ontology (CTDMO) is used as a reference ontology 101 and as a basis for describing the data target database 107. For each data source 102 a different ontology 104 is implemented. However, in some embodiments the CTDMO as well as the data source ontology 104 follow the same modeling rules.

The ontologies may be modeled in the OWL Lite language. Properties which do not represent relationships are modeled as data attributes in the ontologies and have to have a data type assigned. Relationships between concepts have to be modeled in the ontologies as object properties. A 1:n-relationship is represented by a functional object property. The object property has to be defined at the n-side concept of the relation. A 1:1-relationship is modeled as a functional and inverse functional object property and assigned to the n-side concept of the relationship. An n:m-relationship is modeled as an object property which has no restrictions. The property can be assigned to the one or the other side. For each of the object properties the referenced concept has to be defined.

In an embodiment, a user interface is provided for assisting a user to create the data source ontologies 104, 105.

In an embodiment a user can create new data integration modules, e.g. SQL Server™ Integration Service packages, by providing a number of links between the data source ontology 104 and specific concepts selected from the CTDMO 101, and additional information.

In an embodiment, the data integration module is a description that defines among others file, database and data handling to integrate data from different sources 102 into one target 107. To create the data integration module, the user links properties of the data source ontology 102 concepts to properties of the selected concepts of the CTDMO in a visual way.

After providing some additional information for the new module, a web service will create the package based on the mappings and the additional information automatically. Here, additional information may comprise a scheduling of the execution of the data integration module, the handling of files (if the data source is of a file type), e.g. copying and deleting files from a remote location, archiving of files.

Figure 3:
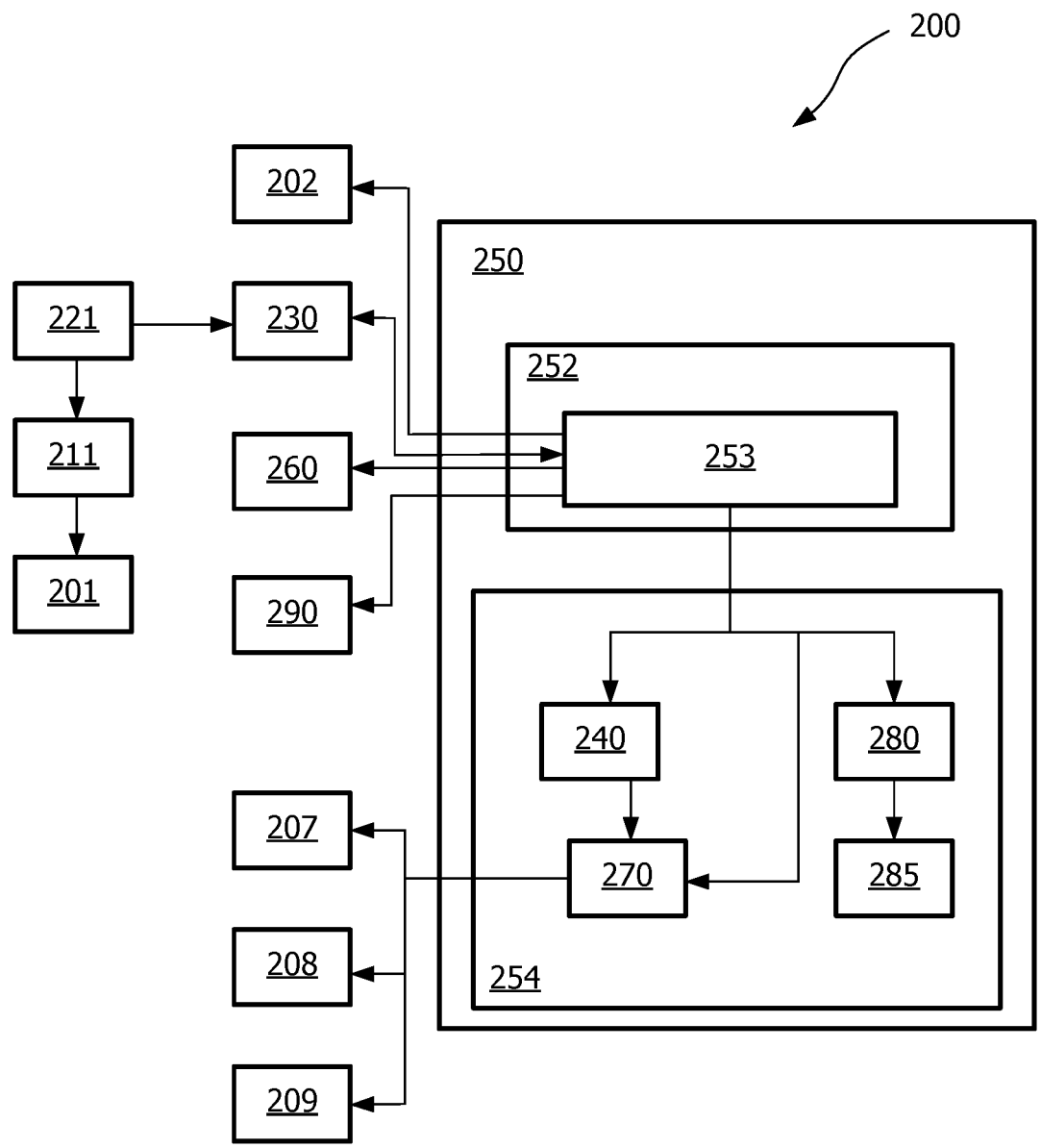
FIG. 3 is a block diagram schematically showing a method according to an embodiment.

FIG. 3 shows an architecture 200 implementing an embodiment of a method 100. The architecture 200 is based on the CTDMO as a reference ontology 201. However, any other ontology following the same modeling rules may be used. The CTDMO 201 may be extended for each new clinical study by means of an ontology editor 211. Data sources 207, 208, 209 are described by data source ontologies 202, and the target database 240 is defined by the CTDMO 201, or parts of it. A user 221 selects concepts from the reference ontology 201 in a user interface 230 to create a relational schema for a clinical study database 240. A mapping between a selection of the reference ontology 201 and the data source ontologies 202 is converted into data integration modules. A web service 253, comprised in a web server 252 handles the generation of database schemas and data integration modules 280 and optionally stores them in a database or in the file system. This is provided by means of a database server 254 comprising a data integration facility 270 processing the data integration modules 280.

Depending on a mapping between concepts and properties of two ontologies, data integration modules may be assembled, i.e., processes to extract data from data sources 207, 208, 209 and load them into a data target 240. Here, both the data sources 207, 208, 209 and the data target 240 are described by separate ontologies 201, 202. A meta representation 260 links the relational and the ontological representation of the data sources 207, 208, 209 and the data target 240. It is assumed that each one of the data source 207, 208, 209 can be represented in a relational way. The web server 252 and the database server 254 are comprised within an application server 250. However, the web server 252 and the database server 245 may also be installed on two separate servers.

Figure 4:
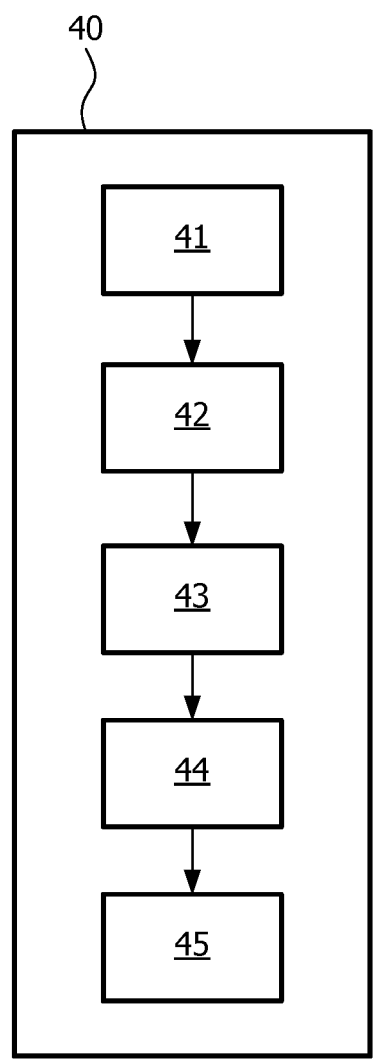
FIG. 4 is a block diagram schematically showing a module according to an embodiment.

In an embodiment, according to FIG. 4, a module 40 is provided. The module comprises a first unit 41 for accessing a target database 107 comprising at least one table associated with a first concept or property of a reference ontology 101. The module further comprises a second unit 42 for defining a data source ontology for a data source ontology 104 for a data source 102 comprising a dataset, said data source ontology 104 comprising a second concept or property, wherein said second concept or property is different from said first concept or property. Moreover, the module comprises a third unit 43 for creating a link between said second concept or property and said first concept or property, said link defining to which table of said target database data of said dataset, associated with said second concept or property, is related.

In an embodiment the module further comprises a unit 44 for creating a data integration module and storing said link into the data integration module. The module may further comprise a unit 45 for storing said data into the corresponding table of the target database 107.

In an embodiment, the unit 45 is configured to execute the created data integration modules. Hence, data is extracted from the data source 102 and loaded into the target database 107.

In an embodiment the third unit 43 for creating a link is connected to a user interface for manually linking concepts or properties of the data source ontology 104 to one concept or property of the reference ontology 101.

In an embodiment, a computer program product is provided. The computer program is stored on a computer-readable medium comprising software code implemented to perform the steps of the method 100 according some embodiments when executed on a data-processing apparatus.

The invention may be implemented in any suitable form including hardware, software, firmware or any combination of these. However, preferably, the invention is implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

It will be appreciated that the embodiments described in the foregoing may be combined without departing from the scope as defined by the appended patent claims.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A computer-readable, non-transitory medium storing software code representing instructions that when executed by a computing system cause the computing system to perform a method of linking data of a data source to a target database, the method comprising:
receiving a target database comprising at least one table associated with a first concept or property of a reference ontology, wherein the target database is defined by a user-selected first set of concepts or properties of the reference ontology;
generating a data source ontology associated with a second set of concepts or properties of a data source ontology, the second set of concepts or properties being different from the first set of concepts or properties;
creating a link between said first set of concepts or properties and said second set of concepts or properties that relates the second set of concepts or properties to the table of the target database; and
integrating data into the target database based on the created link.

2. The computer-readable, non-transitory medium according to claim 1, wherein integrating comprises storing the data in the target database.

3. The computer-readable, non-transitory medium according to claim 1, further comprising storing said link into a data integration module.

4. The computer-readable, non-transitory medium according to claim 1, wherein creating said link further comprises mapping the first set of concepts or properties and the second set of concepts or properties based on relational queries.

5. The computer-readable, non-transitory medium according to claim 1, wherein creating said link further comprises assembling a query on the second set of concepts or properties.

6. The computer-readable, non-transitory medium according to claim 1, wherein generating the data source ontology further comprises providing a user interface for converting a relational schema representation of the data source to an ontology.

7. The computer-readable, non-transitory medium according to claim 1, further comprising linking an ontological representation of the target database with a relational representation of the target database.

8. The computer-readable, non-transitory medium according to claim 1, further comprising linking an ontological representation of a data source with a relational representation of the data source.

9. The computer-readable, non-transitory medium according to claim 8, wherein linking the ontological representations with the relational representations further comprises recording a relationship by means of meta representations.

10. The computer-readable, non-transitory medium according to claim 9, wherein linking the ontological representations with the relational representations further comprises recording a relationship by means of meta representations.

11. The computer-readable, non-transitory medium according to claim 1, wherein the data comprises medical data of a clinical trial.

* * * * *